US006390999B1

(12) United States Patent
Zscheile et al.

(10) Patent No.: US 6,390,999 B1
(45) Date of Patent: May 21, 2002

(54) METHOD AND APPARATUS FOR FLOW MEASUREMENT WITH TEMPERATURE AND DENSITY COMPENSATION

(75) Inventors: John Zscheile, Rockledge, FL (US); Jeffrey F. Puckett, Rector, AR (US); Richard S. Eidens, Salt Lake City, UT (US)

(73) Assignee: Rocky Mountain Research, Inc., Salt Lake City, UT (US)

( * ) Notice: Subject to any disclaimer, the term of this patent is extended or adjusted under 35 U.S.C. 154(b) by 0 days.

(21) Appl. No.: 08/882,948

(22) Filed: Jun. 26, 1997

Related U.S. Application Data
(60) Provisional application No. 60/020,867, filed on Jun. 28, 1996.

(51) Int. Cl.[7] ............................................. A61M 37/00
(52) U.S. Cl. .................................. 604/4.01; 73/861.29
(58) Field of Search ....................... 604/246, 4.01–6.14; 327/231, 327, 262; 73/861.27–861.29

(56) References Cited

U.S. PATENT DOCUMENTS

| | | | |
|---|---|---|---|
| 3,727,454 A | 4/1973 | Courty | |
| 4,052,896 A | 10/1977 | Lee et al. | |
| 4,227,407 A | 10/1980 | Drost | |
| 4,452,090 A | 6/1984 | Kou et al. | |
| 4,488,428 A | 12/1984 | Taniuchi | |
| 4,555,947 A | 12/1985 | Van Prooijen | |
| 4,596,133 A | 6/1986 | Smalling et al. | |
| 4,611,496 A | 9/1986 | Komachi | |
| 4,923,598 A | * 5/1990 | Sehäl | |
| 5,052,230 A | 10/1991 | Lang et al. | |
| 5,152,174 A | 10/1992 | Labudde | |
| 5,445,613 A | 8/1995 | Orth | |

* cited by examiner

Primary Examiner—Mark Bockelman
(74) Attorney, Agent, or Firm—TraskBritt

(57) ABSTRACT

A transit time ultrasonic flow meter includes a pair of ultrasonic transducers transmitting an ultrasonic signal through a fluid flowing in a conduit and receiving the transmitted ultrasonic signal. An exclusive-OR (XOR) phase comparator then detects a difference in phase between the received ultrasonic signal and a reference signal having a selected phase shift (e.g., 0°, 90°, 180°, or 270°) with respect to the transmitted ultrasonic signal. Control circuitry selects the phase shift of the reference signal based on outputs of the XOR phase comparator in order to maintain the phase shifts detected by the XOR phase comparator within a range in which the comparator has relatively accurate detection (e.g., 45° to 135°). By adjusting the phase of the reference signal and thereby maintaining the XOR phase comparator in its relatively high accuracy region, the present invention enhances the accuracy of detection by the phase comparator. Since the outputs of the phase comparator are correlated to fluid flow, adjusting the phase of the reference signal also enhances the inventive flow meter's measurement of fluid flow. The present invention also provides what is commonly referred to as an air-in-line detector, which is used, for example, to detect air bubbles in an extracorporeal blood line to prevent introducing air into a patient's circulatory system.

33 Claims, 14 Drawing Sheets

METHOD AND APPARATUS FOR FLOW MEASUREMENT WITH TEMPERATURE AND DENSITY COMPENSATION

This patent application claims the benefit under 35 U.S.C. §119(e) of the Jun. 28, 1996 filing date of U.S. provisional patent application No. 60/020,867.

BACKGROUND OF THE INVENTION

1. Field of the Invention

This invention pertains to the measurement of fluid flow in a conduit, with compensation for variations in the temperature and density of the fluid. The invention has a wide range of specific applications, including, for example, monitoring of blood flowing outside the body of a patient through tubing during medical procedures, measurement of the velocity of a ship or other vessel traveling through water, monitoring of the flow of petroleum materials to a flare stack in a petroleum production or refining facility, measurement of the flow of air or fuel to an engine, measurement of the flow of hydrocarbon fluids from a well head, storage tank or pump, and measurement of fluid flow in a chemical-carrying conduit. In addition, the invention has general applicability in many fields, including, for example, medicine, biology, automobiles, aerospace, the military, oceanography, meteorology, cryogenics, pharmacology, chemical production and processing, agriculture, and the oil and gas industry.

2. State of the Art

With reference to FIG. 1A, a well-known technique for measuring the flow (denoted by arrows) of a fluid 8 through a conduit 10 is commonly referred to as "transit time" flow metering. In this technique, transducer driving signals 12 and 14 cause a downstream ultrasonic transducer 16 to emit an ultrasonic signal 18 that traverses the conduit 10 and the fluid 8 and is received by an upstream ultrasonic transducer 20. Because the ultrasonic signal 18 takes time to pass through the conduit 10 and the fluid 8, transducer output signals 22 and 24 indicative of the received ultrasonic signal 18 lag behind the transducer driving signals 12 and 14 by an upstream phase shift $\Delta\phi_{upstream}$.

As shown in FIG. 1B, every few milliseconds, the roles of the upstream and downstream transducers 20 and 16 are reversed so that the transducer driving signals 12 and 14 cause the upstream transducer 20 to emit an ultrasonic signal 28 that traverses the conduit 10 and the fluid 8 and is received by the downstream transducer 16. Because the ultrasonic signal 28 takes time to pass through the conduit 10 and the fluid 8, transducer output signals 30 and 32 indicative of the received ultrasonic signal 28 lag behind the transducer driving signals 12 and 14 by a downstream phase shift $\Delta\phi_{downstream}$.

When the fluid 8 is not flowing, the upstream and downstream phase shifts $\Delta\phi_{upstream}$ and $\Delta\phi_{downstream}$ equal one another and are attributable solely to properties of the fluid 8 other than flow (primarily temperature, density, and compressibility). Thus, under this condition, $$\Delta\phi_{upstream} = \Delta\phi_{downstream} = \Delta\phi_{fluid} \quad (1)$$

where $\Delta\phi_{fluid}$ is the phase shift attributable to properties of the fluid 8 other than flow.

When, instead, the fluid 8 is flowing, the upstream and downstream phase shifts $\Delta\phi_{upstream}$ and $\Delta\phi_{downstream}$ do not equal one another. Rather, the upstream phase shift $\Delta\phi_{upstream}$ includes an additional component $\Delta\phi_{up\_flow}$ attributable to the additional time the ultrasonic signal 18 takes to traverse upstream against the flowing fluid 8, while the downstream phase shift $\Delta\phi_{downstream}$ is reduced by a component $\Delta\phi_{down\_flow}$ attributable to the ultrasonic signal 28 being aided by traversing downstream with the flowing fluid 8. Thus, $$\Delta\phi_{upstream} = \Delta\phi_{fluid} + \Delta\phi_{up\_flow} \quad (2)$$

$$\Delta\phi_{downstream} = \Delta\phi_{fluid} - \Delta\phi_{down\_flow} \quad (3)$$

The components $\Delta\phi_{up\_flow}$ and $\Delta\phi_{down\_flow}$ may be defined as follows:

$$\Delta\phi_{up\_flow} = (2\pi f \times s)/(c+(r_f \times \cos(\theta))) \quad (4)$$

$$\Delta\phi_{down\_flow} = (2\pi f \times s)/(c-(r_f \times \cos(\theta))) \quad (5)$$

where f is the frequency of the ultrasonic signals 18 and 28, s is the distance shown in FIGS. 1A and 1B between the transducers 16 and 20, c is the speed of sound in the fluid 8, $r_f$ is the rate of flow of the fluid 8 in the conduit 10, and the angle θ is the angle shown in FIGS. 1A and 1B between the axis of transmission of the ultrasonic signals 18 and 28 and the longitudinal axis of the conduit 10.

As shown in FIG. 1C, taking the difference between the downstream phase shift $\Delta\phi_{downstream}$ and the upstream phase shift $\Delta\phi_{upstream}$ using a differential amplifier 34 cancels out the phase shift $\Delta\phi_{fluid}$ and yields the sum of the phase shift components $\Delta\phi_{up\_flow}$ and $\Delta\phi^{down}_{flow}$ as the output $\Delta\phi_{flow}$ of the amplifier 34. Thus, $$\Delta\phi_{upstream} - \Delta\phi_{downstream} = \Delta\phi_{fluid} + \Delta\phi_{up\_flow} - (\Delta\phi_{fluid} - \Delta\phi_{down\_flow}) = \Delta\phi_{flow} \quad (6)$$

$$= \Delta\phi_{up\_flow} + \Delta\phi_{down\_flow} = \Delta\phi_{flow} \quad (7)$$

Since the phase shift components $\Delta\phi_{up\_flow}$ and $\Delta\phi_{down\_flow}$ are related to fluid flow $r_f$ (see equations (4) and (5) above), it may be said that $$r_f = f(\Delta\phi_{flow}, f, s, c, \theta) \quad (8)$$

Thus, with appropriate correlation of the output $\Delta\phi_{flow}$ of the differential amplifier 34 to the fluid flow $r_f$ using calibrated circuitry, the fluid flow $r_f$ may be determined.

A conventional transit time flow metering system like that discussed above is described in more detail in U.S. Pat. No. 4,227,407 to Drost. Also, applications for conventional transit time flow metering systems like that described above are found in a wide variety of contexts, including measuring petroleum materials flowing to a flare stack, as described in U.S. Pat. No. 4,596,133 to Smalling et al., measuring air flowing to an automobile engine, as described in U.S. Pat. No. 4,488,428 to Taniuchi, and monitoring blood flowing outside the body of a patient ("extracorporeal blood flow") through tubing during medical procedures to actuate a clamp on the tubing, if necessary, to prevent back-flow flow of the blood, as described in U.S. Pat. No. 5,445,613 to Orth (assigned to the Assignee of the present invention, Rocky Mountain Research, Inc. of Salt Lake City, Utah).

While conventional transit time flow metering systems are useful in a variety of contexts, they traditionally lack the accuracy necessary or desirable in some instances. For example, while state-of-the-art transit time flow metering systems can be accurate to within ±2%, some applications, like extracorporeal blood flow monitoring, would benefit from accuracies within ±1%. Transit time flow metering systems traditionally lack greater accuracy because the above-described process of correlating the value $\Delta\phi_{flow}$ to fluid flow is subject to errors resulting primarily from variations in the temperature and density of the fluid being measured.

Therefore, there is a need in the art for a transit time ultrasonic fluid flow metering apparatus and method with compensation for variations in the temperature and density of the fluid for enhanced accuracy. Such an apparatus and method should have applicability in a wide variety of flow metering contexts.

SUMMARY OF THE INVENTION

An inventive transit time flow meter includes an assembly for transmitting an ultrasonic signal through fluid in a conduit and for receiving the transmitted ultrasonic signal. The assembly may comprise a pair of ultrasonic transducers. Circuitry coupleable to the transmitting and receiving assembly detects phase shifts in the received ultrasonic signal relative to the transmitted ultrasonic signal, and circuitry coupled to the phase shift detecting circuitry adjusts future detection of such phase shifts in response to already-detected phase shifts to enhance the accuracy of such future detection. Thus, the present invention uses feedback during the detection of phase shifts indicative of the flow of the fluid in the conduit to enhance future detection of such phase shifts and thereby enhance accurate correlation of the phase shifts to fluid flow.

As an example, the phase shift detecting circuitry may include an exclusive-OR (XOR) phase comparator having a limited range of relatively high accuracy, such as between 45° and 135°. The adjusting circuitry then includes feedback circuitry for maintaining the phase shifts detected by the XOR phase comparator within its limited range to enhance the accuracy of the comparator's detections, thus enhancing accurate correlation of the detected phase shifts to fluid flow.

An inventive apparatus for conducting a fluid while metering flow of the fluid includes a fluid conduit through which the fluid may flow and the above-described flow meter. The conduit may be, for example, tubing (e.g., Tygon® tubing), a water conduit on a hull of a vessel, a flare stack inlet pipe, an air inlet of an engine, a fuel inlet of an engine, a pipeline, a drilling rig conduit, or a conduit used in a chemical process.

In a preferred embodiment, an extracorporeal blood flow system includes a blood conduit connectable to a patient for diverting blood from, and later returning blood to, the patient, a pump connectable in-line with the blood conduit for pumping blood therethrough, and the flow meter described above. The system may also include one or more powered clamps attached to the blood conduit for clamping the conduit closed.

In another embodiment, flow metering circuitry for use in a flow metering apparatus having the ultrasonic transmitting and receiving assembly described above includes circuitry for starting a transit time count upon the initiation of transmission of an ultrasonic signal through the fluid and for stopping the transit time count upon reception of the transmitted ultrasonic signal. The count circuitry may be, for example, a digital counter. The flow metering circuitry may also include circuitry for correlating transit time counts by the count circuitry to flows or temperatures of the fluid, thus allowing for determination of the fluid flows or the temperature of the fluid.

In still another embodiment, an apparatus for detecting anomalies, such as air bubbles in a fluid such as blood flowing in a conduit, includes the above-described ultrasonic transmitting and receiving assembly. Circuitry coupleable to the transmitting and receiving assembly outputs an anomaly detection signal that changes relatively rapidly in response to variations in the amplitude of the received ultrasonic signal. Such circuitry may include an amplifier and a Resistor-Capacitor (RC) network. Sample-and-hold circuitry coupleable to the transmitting and receiving assembly samples the amplitude of the received ultrasonic signal and outputs another anomaly detection signal that changes relatively slowly in response to variations in the amplitude. Circuitry coupled to the rapidly changing anomaly detection signal outputting circuitry and the sample-and-hold circuitry then detects differences between the rapidly changing and slowly changing anomaly detection signals indicative of anomalies in the fluid.

Various methods of the present invention correspond to the structures described above. One such method—a method of measuring the temperature of a fluid in a conduit—includes transmitting an ultrasonic signal through the fluid. The ultrasonic signal is then received, and phase shifts in the received signal relative to the transmitted signal are detected. The detected phase shifts are then correlated to the temperature of the fluid, and the detection of the phase shifts is adjusted in response to previously detected phase shifts to enhance the accuracy of the correlation of detected phase shifts to the temperature of the fluid.

DETAILED DESCRIPTION OF THE ILLUSTRATED EMBODIMENTS

Figure 1A:
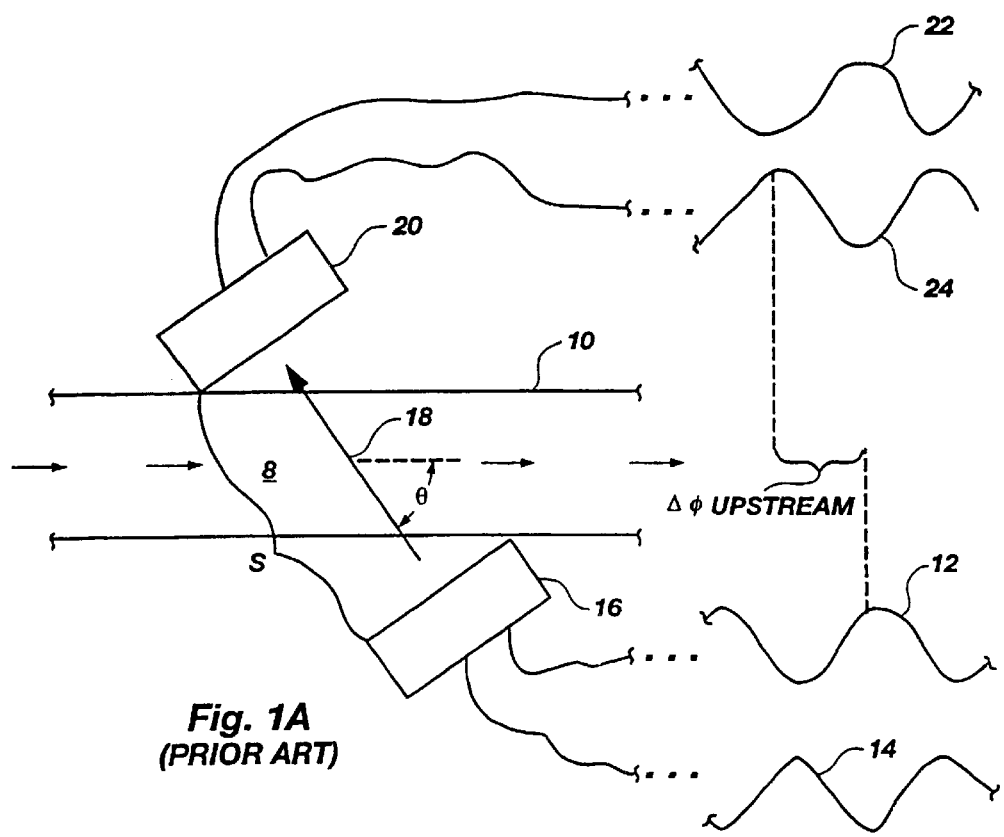
FIGS. 1A, 1B, and 1C are schematic and graphical representations of conventional ultrasonic transit time flow metering.
Figure 1B:
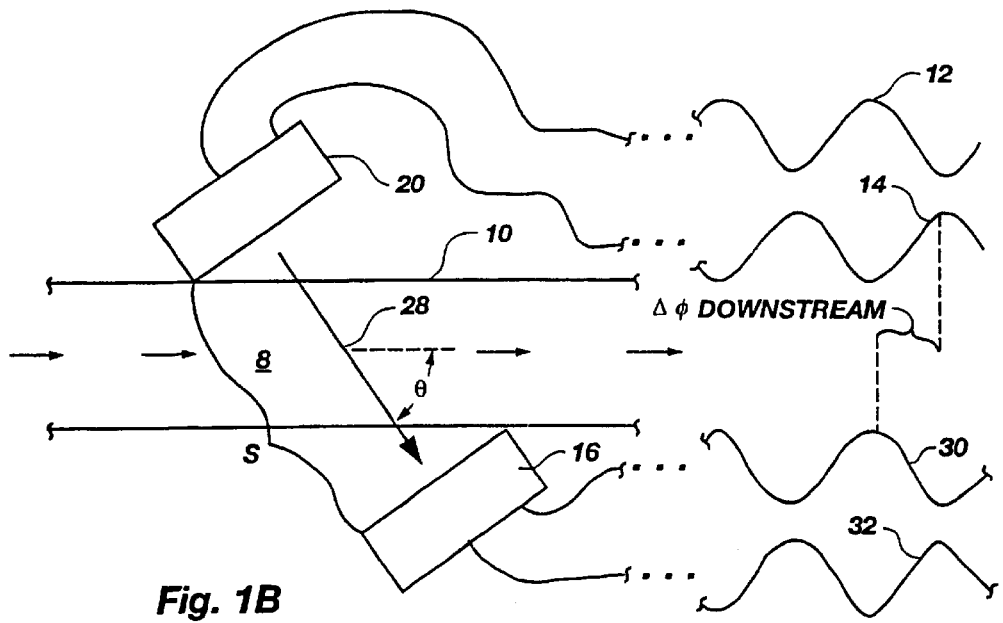
Figure 1C:
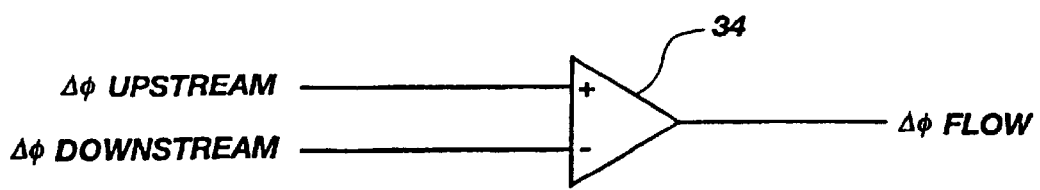
Figure 2:
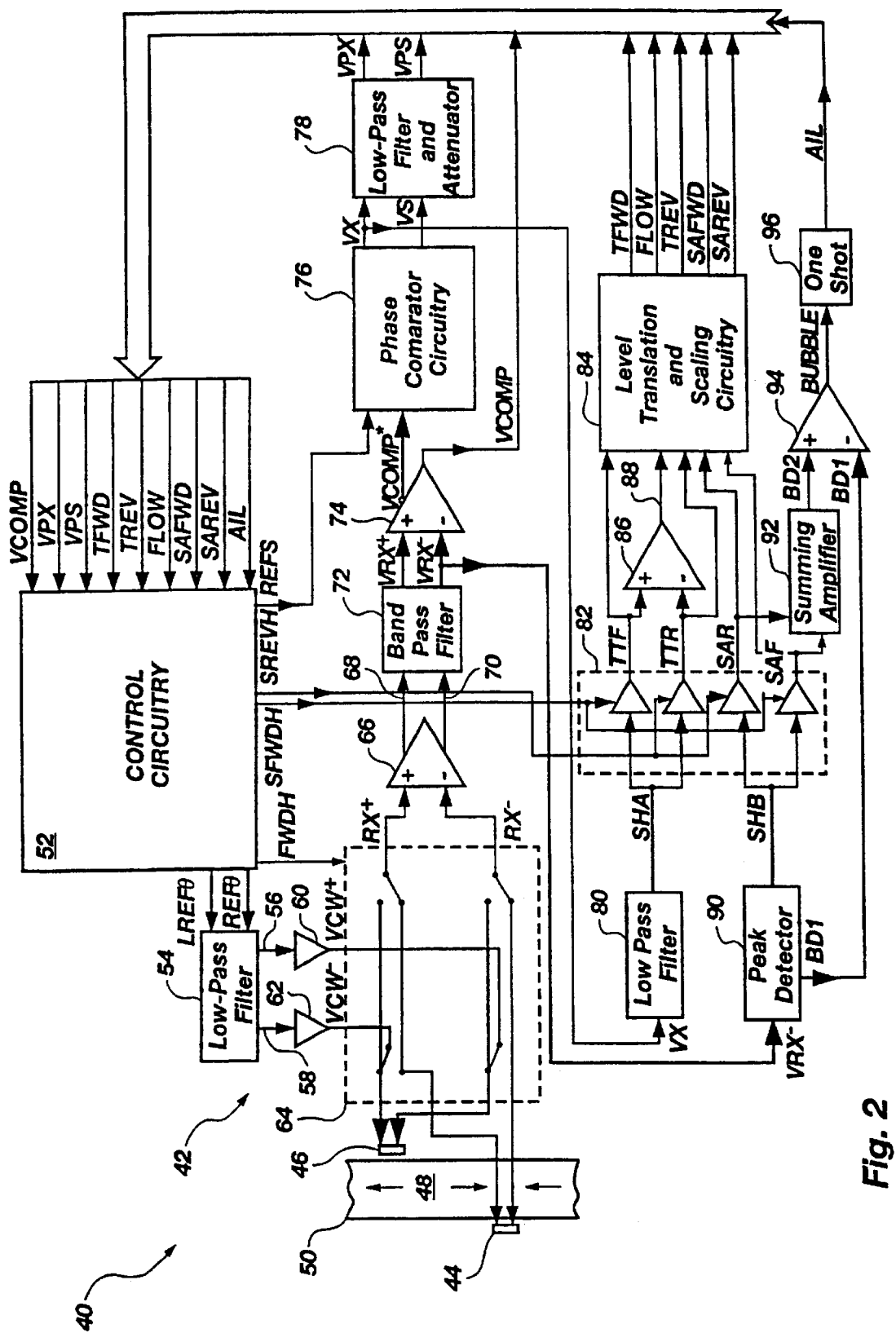
FIG. 2 is a block diagram of a flow metering circuit in accordance with the present invention.

As shown in FIG. 2, an ultrasonic transit time flow meter 40 having enhanced accuracy in accordance with the present invention includes a flow metering circuit 42 and upstream and downstream ultrasonic transducers 44 and 46 for measuring the flow (denoted by arrows) of a fluid 48 in a conduit 50. It should be understood that the present invention is intended for use with any fluid, including, for example, blood, air, fuel, petroleum, natural gas, mud, water, and any other liquid or gas. It should also be understood that the present invention may be used with any conduit, including, for example, tubing, a conduit in or on the hull of a vessel for measuring the velocity of the vessel through water, a feeder pipe for a flare stack in a petroleum production or refining operation, an air or fuel inlet conduit to an engine, an effluent line from a petroleum or other drilling rig, a conduit for hydrocarbon fluids from a well-head, storage tank, or pump, a chemical process conduit, or any open-channel conduit.

General Operation of the Flow Metering Circuit

Control circuitry 52 in the flow metering circuit 42 provides a 2.5 Megahertz (MHZ) square-wave timing signal REF0, and its inverse LREF0, to a low-pass filter 54. Filtered outputs 56 and 58 from the low-pass filter 54, corresponding to the REF0 and LREF0 signals, are then amplified by current drivers 60 and 62 and output as transducer driver signals VCW$^+$ and VCW$^-$ to a quad single-pole double-throw transmit/receive T/R) switch 64. Referring to the timing diagram of FIG. 3 for a moment, examples of the timing signal REF0 and its inverse LREF0, and the corresponding transducer driver signals VCW$^+$ and VCW$^-$, are shown therein. It should be understood that the various signal frequencies described herein, including the 2.5 MHZ frequency of the REF0 and LREF0 signals, are exemplary only, and that the flow metering circuit 42 (FIG. 2) may be operated at a wide variety of signal frequencies. The control circuitry 52 will be described in more detail below with respect to FIGS. 11A and 11B.

Referring again to FIG. 2, the T/R switch 64 is shown therein in an upstream switching state in which the transducer driver signals VCW$^+$ and VCW$^-$ drive the downstream transducer 46 to emit an ultrasonic signal (not shown) that traverses upstream through the conduit 50 and the flowing fluid 48 and is received by the upstream transducer 44. Because of the upstream switching state of the T/R switch 64, output signals from the upstream transducer 44 induced by reception of the transmitted ultrasonic signal appear as switch output signals RX$^+$ and RX$^-$ for presentation to a receiver amplifier 66. Output signals 68 and 70 from the amplifier 66 then pass through a 2.5 MHZ band-pass filter 72 and emerge as filtered output signals VRX$^+$ and VRX$^-$ for presentation to a zero-crossing detector 74.

A 152 Hz square-wave switching signal FWDH from the control circuitry 52 periodically switches the T/R switch 64 between the upstream switching state described above and a downstream switching state (not shown in FIG. 2) in which the transducer driver signals VCW$^+$ and VCW$^-$ drive the upstream transducer 44 to emit an ultrasonic signal (not shown) that traverses downstream through the conduit 50 and the flowing fluid 48 and is received by the downstream transducer 46. Because of the downstream switching state of the T/R switch 64, output signals from the downstream transducer 46 induced by reception of the transmitted ultrasonic signal then appear as the switch output signals RX$^+$ and RX$^-$ for presentation to the receiver amplifier 66. The output signals 68 and 70 from the amplifier 66 then pass through the band-pass filter 72 and emerge as the filtered output signals VRX$^+$ and VRX$^-$ for presentation to the zero-crossing detector 74.

Figure 3:
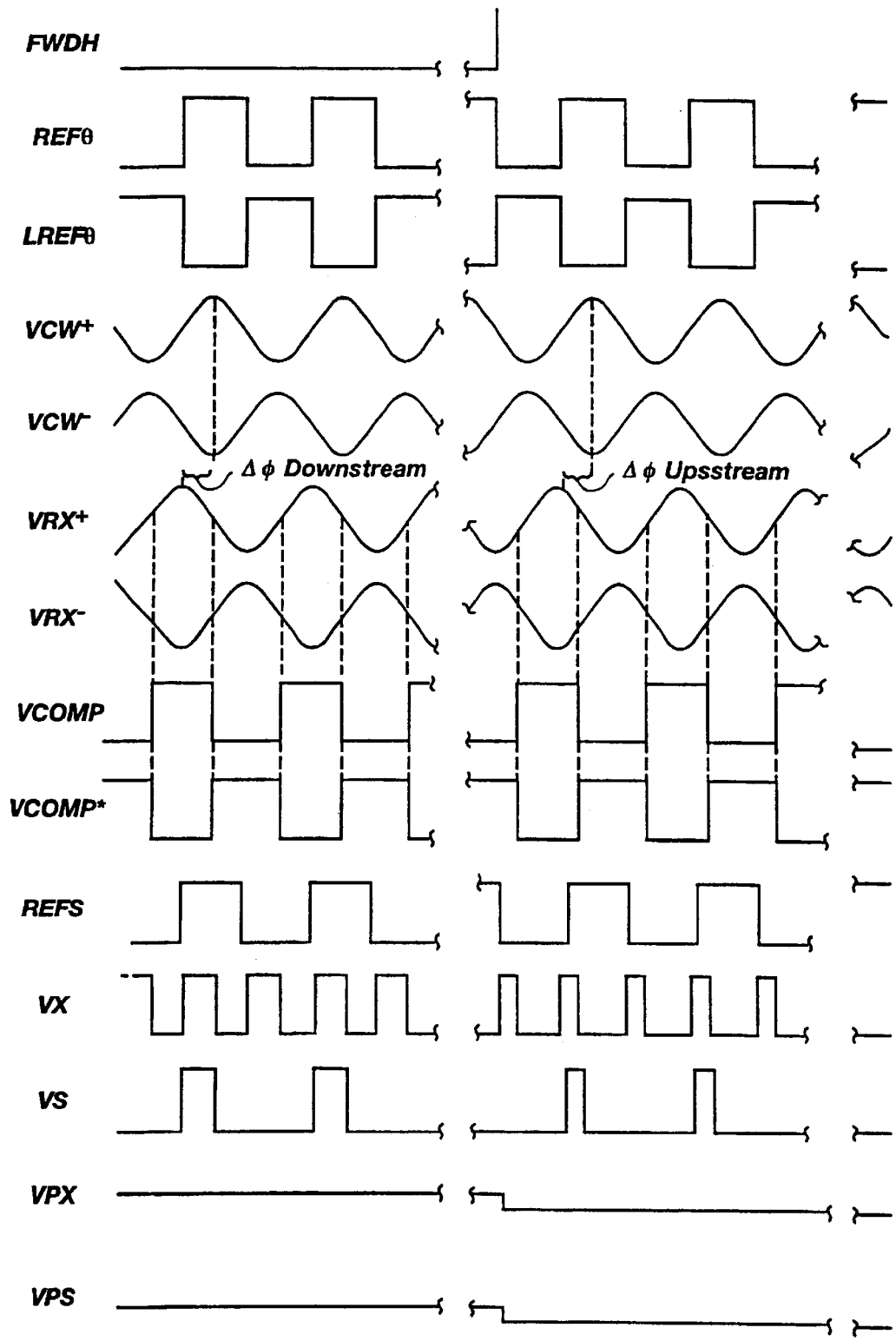
FIG. 3 is a timing diagram showing operation of phase comparator circuitry in the flow metering circuit of FIG. 2.

Referring to FIG. 3, examples of the switching signal FWDH and the filtered output signals VRX$^+$ and VRX$^-$ are shown therein. When the switching signal FWDH is low, the T/R switch 64 (FIG. 2) is in its downstream switching state, so a downstream phase shift $\Delta\phi_{downstream}$ develops between the transducer driver signal VCW$^+$ and the filtered output signal VRX$^+$. Similarly, when the switching signal FWDH is high, the T/R switch 64 is in its upstream switching state, so an upstream phase shift $\Delta\phi_{upstream}$ develops between the transducer driver signal VCW$^+$ and the filtered output signal VRX$^+$. As discussed above, the upstream phase shift $\Delta\phi_{upstream}$ is greater than the downstream phase shift $\Delta\phi_{downstream}$ when the fluid 48 (FIG. 2) is flowing, and is substantially equal to the downstream phase shift $\Delta\phi_{downstream}$ when the fluid 48 is still.

"Coarse" Temperature/Density Compensation in the Flow Metering Circuit

Referring again to FIG. 2, the zero-crossing detector 74 switches its outputs—a crossing detect signal VCOMP and its compliment VCOMP*—from low to high or from high to low at each mutual zero crossing of the filtered output signals VRX$^+$ and VRX$^-$. This is shown in more detail in the timing diagram of FIG. 3.

The signal VCOMP*, representing the upstream or downstream phase shift $\Delta\phi_{upstream}$ or $\Delta\phi_{downstream}$ depending on the switching state of the T/R switch 64, is then compared in phase comparator circuitry 76 to a reference signal REFS from the control circuitry 52. As illustrated in FIG. 3, the reference signal REFS is in phase with the timing signal REF0, although it may, instead, be out of phase with the timing signal REF0 by 90°, 180° or 270°, as will be explained in more detail below with respect to FIGS. 2, 4, and 5A to 5E.

Figure 10:
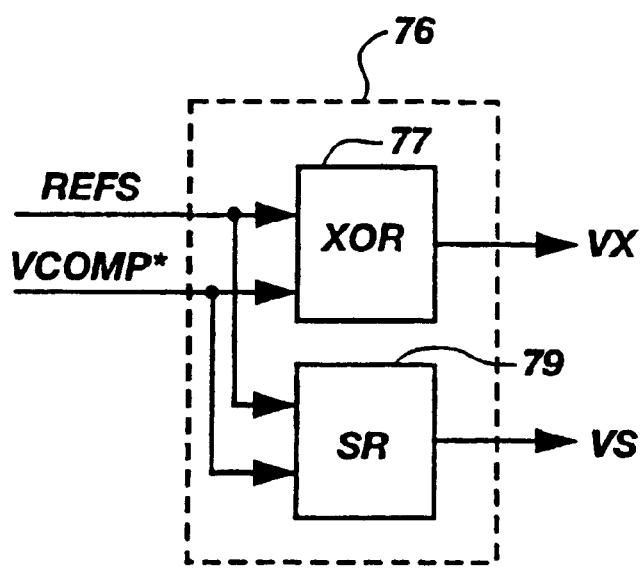
FIG. 10 is a block diagram showing the XOR phase comparator and the SR flip-flop phase comparator in the flow metering circuit of FIG. 2.

Referring again to FIG. 2, an exclusive-OR (XOR) phase comparator within the phase comparator circuitry 76 outputs an XOR phase comparison signal VX at a high level whenever the signal VCOMP* and the reference signal REFS are at different voltage levels. At the same time, a positive edge-triggered Set-Reset (SR) flip-flop phase comparator within the phase comparator circuitry 76 sets its SR phase comparison signal VS at each positive edge of the reference signal REFS and resets its SR phase comparison signal VS at each positive edge of the signal VCOMP*. The XOR phase comparison signal VX and the SR phase comparison signal VS are shown in more detail in FIG. 3. The XOR phase comparator and the SR flip-flop phase comparator, denoted by 77 and 79, are shown in more detail in FIG. 10.

A low-pass filter and attenuator 78 outputs averaged XOR and SR phase comparison signals VPX and VPS to the control circuitry 52. These signals represent an average over time of the highs and lows of the respective XOR and SR phase comparison signals VX and VS. Thus, for example, as shown in FIG. 3, in the downstream switching state of the T/R switch 64 (FIG. 2), the XOR phase comparison signal VX is high about 50% of the time. Accordingly, the averaged XOR phase comparison signal VFX is at about 50% of its potential amplitude. Similarly, the SR phase comparison signal VS is high about 25% of the time, so the averaged SR phase comparison signal VPS is at about 25% of its potential amplitude.

Figure 4:
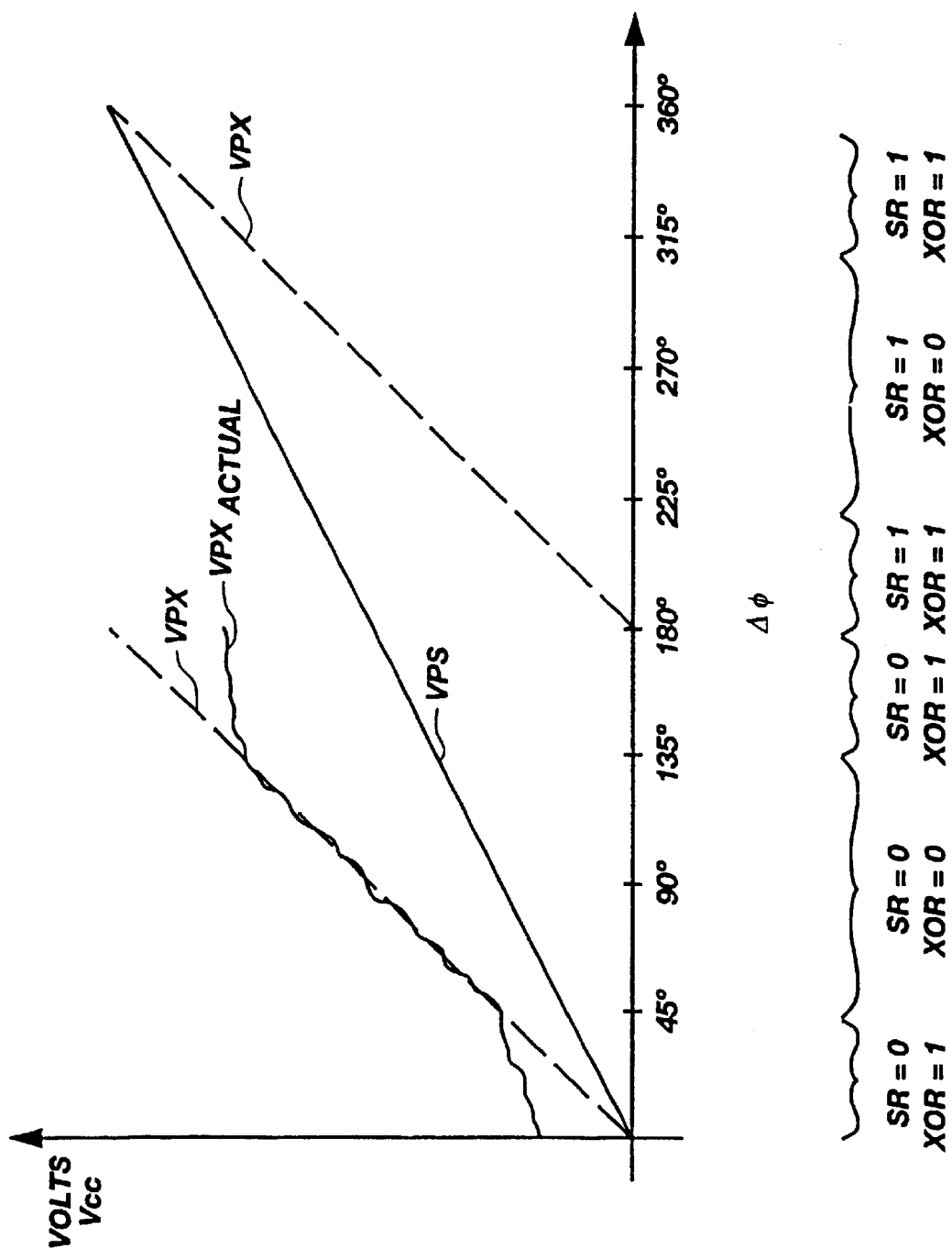
FIG. 4 is a graph of the output voltages of an exclusive-OR (XOR) phase comparator and a Set-Reset Flip-Flop phase comparator in the flow metering circuit of FIG. 2 versus phase shift detected by the comparators.

The averaged XOR and SR phase comparison signals VPX and VPS are shown in more detail in FIG. 4 in a graph of the signals VPX and VPS versus detected phase shift $\Delta\phi$ (upstream or downstream). Also shown in FIG. 4 is a graph of the actual performance of the signal VPX (denoted by $VPX_{actual}$ in FIG. 4) indicative of the actual performance expected of the XOR phase comparator. The present invention recognizes that the XOR phase comparator has non-ideal behavior that gives it only a limited region of relatively accurate response between detected phase shifts Δϕ of about 45° and about 135°. Outside this 45° to 135° range, the accuracy of the XOR phase comparator deteriorates rapidly.

Therefore, the sent invention provides what may be referred to as a "coarse" adjustment to the reference signal REFS provided to the XOR phase comparator to maintain the phase shift αϕ detected by the comparator between 45° and 135°. Referring once again to FIG. 2, based on the amplitudes of the averaged XOR and SR phase comparison signals VPX and VPS, and hence on the phase shift Δϕ detected by the comparators, the control circuitry 52 categorizes the state of the XOR phase comparator and the SR flip-flop phase comparator as "good" or "bad" and selects a reference signal REFS accordingly that is 0°, 90°, 180°, or 270° out of phase with the timing signal REF0 in order to maintain the phase shift Δϕ detected by the XOR phase comparator between 45° and 135°. These states, and the corresponding reference signal REFS phase shift Δϕ, are illustrated in FIG. 4 and in the following table:

TABLE 1

| Detected Δϕ | SR | XOR | REFS Δϕ |
|---|---|---|---|
| 45° to 135° | 0 (good) | 0 (good) | 0° |
| 0° to 45° and 135° to 180° | 0 (good) | 1 (bad) | 90° |
| 225° to 315° | 1 (bad) | 0 (good) | 180° |
| 180° to 225° and 315° to 360° | 1 (bad) | 1 (bad) | 270° |

Figure 5A:
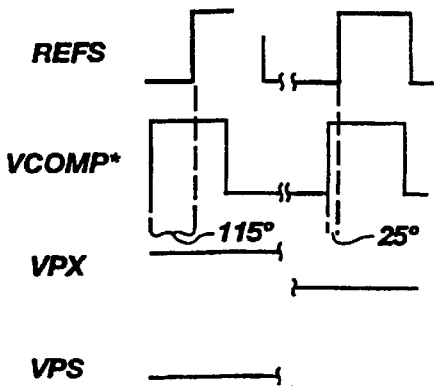
FIGS. 5A, 5B, 5C, 5D, and 5E are tiring diagrams showing "coarse" adjustments to the phase comparator circuitry in the flow metering circuit of FIG. 2 in accordance with the present invention.

Examples of the operation of the coarse adjustment described above are shown in FIGS. 5A to 5E. As shown in FIG. 5A, the amplitudes of the signals VPX and VPS indicate to the control circuitry 52 (FIG. 2) that the phase shift Δϕ detected by the XOR phase comparator and the SR flip-flop phase comparator is about 25°, so the control circuitry 52 categorizes the state of the SR flip-flop phase comparator as good, and the state of the XOR phase comparator as bad. As a result, the control circuitry 52 shifts the phase of the reference signal REPS by 90° relative to the timing signal REF0 so the phase shift Δϕ then detected by the XOR phase comparator and the SR flip-flop phase comparator is well within the accuracy range of the XOR phase comparator at about 115°.

Figure 5B:
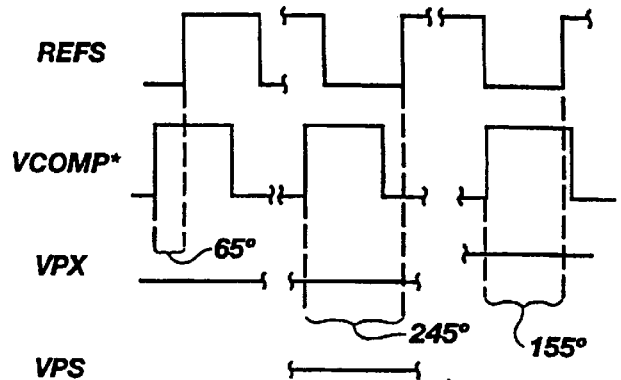

Similarly, as shown in FIG. 5B, the amplitudes of the signals VPX and VPS indicate to the control circuitry 52 (FIG. 2) that the phase shift Δϕ detected by the XOR phase comparator and the SR flip-flop phase comparator is about 155°, so the control circuitry 52 categorizes the state of the SR flip-flop phase comparator as good, and the state of the XOR phase comparator as bad. As a result, the control circuitry 52 shifts the phase of the reference signal REFS by 90° relative to the timing signal REF0 so the phase shift Δϕ then detected by the XOR phase comparator and the SR flip-flop phase comparator is 245°. The control circuitry 52 then categorizes the state of the SR flip-flop phase comparator as bad, and the state of the XOR phase comparator as good, so the control circuitry 52 shifts the phase of the reference signal REFS by 180° relative to the timing signal REF0 so the phase shift Δϕ then detected by the XOR phase comparator and the SR flip-flop phase comparator is well within the accuracy range of the XOR phase comparator at about 65°.

Figure 5C:
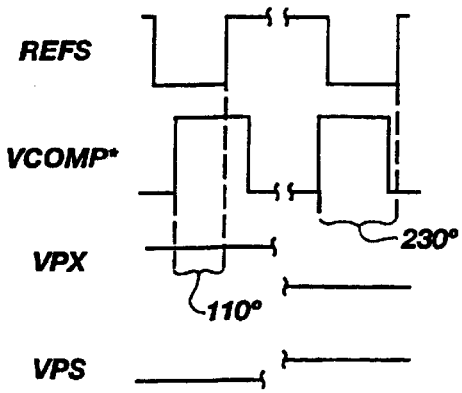

As shown in FIG. 5C, the amplitudes of the signals VPX and VPS indicate to the control circuitry 52 (FIG. 2) that the phase shift Δϕ detected by the XOR phase comparator and the SR flip-flop phase comparator is about 200°, so the control circuitry 52 categorizes the state of the SR flip-flop phase comparator as bad, and the state of the XOR phase comparator as bad. As a result, the control circuitry 52 shifts the phase of the reference signal REFS by 270° relative to the timing signal REF0 so the phase shift Δϕ then detected by the XOR phase comparator and the SR flip-flop phase comparator is well within the accuracy range of the XOR phase comparator at about 110°.

Figure 5D:
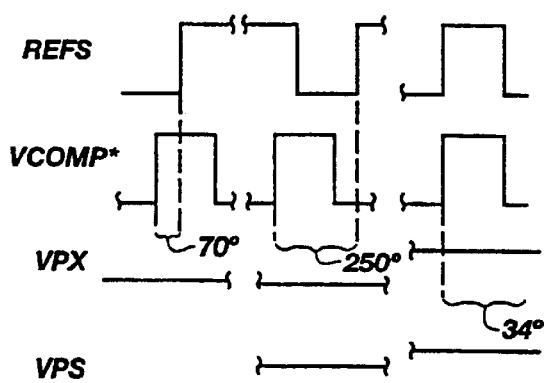

As shown in FIG. 5D, the amplitudes of the signals VPX and VPS indicate to the control circuitry 52 (FIG. 2) that the phase shift Δϕ detected by the XOR phase comparator and the SR flip-flop phase comparator is about 340°, so the control circuitry 52 categorizes the state of the SR flip-flop phase comparator as bad, and the state of the XOR phase comparator as bad. As a result, the control circuitry 52 shifts the phase of the reference signal REFS by 270° relative to the timing signal REF0 so the phase shift Δϕ then detected by the XOR phase comparator and the SR flip-flop phase comparator is 250°. The control circuitry 52 then categorizes the state of the SR flip-flop phase comparator as bad, and the state of the XOR phase comparator as good, so the control circuitry 52 shifts the phase of the reference signal REPS by 180° relative to the timing signal REF0 so the phase shift Δϕ then detected by the XOR phase comparator and the SR flip-flop phase comparator is well within the accuracy range of the XOR phase comparator at about 70°.

Figure 5E:
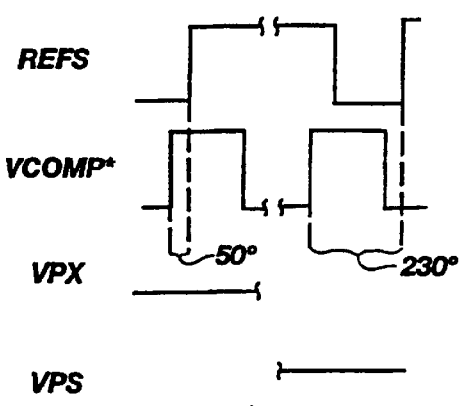

Likewise, as shown in FIG. 5E, the amplitudes of the signals VPX and VPS indicate to the control circuitry 52 (FIG. 2) that the phase shift Δϕ detected by the XOR phase comparator and the SR flip-flop phase comparator is about 230°, so the control circuitry 52 categorizes the state of the SR flip-flop phase comparator as bad, and the state of the XOR phase comparator as good. As a result, the control circuitry 52 shifts the phase of the reference signal REFS by 180° relative to the timing signal REF0 so the phase shift Δϕ then detected by the XOR phase comparator and the SR flip-flop phase comparator is well within the accuracy range of the XOR phase comparator at about 50°.

It should be understood that while the present invention is described with respect to a coarse adjustment in the form of a phase shift of 0°, 90°, 180°, or 270°, the invention is not so limited. Rather, the invention includes within its scope any combination of adjustments which will bring the XOR phase comparator into its range of accuracy. It should also be understood that other phase comparators may be employed with the present invention which have ranges of accuracy other than between 45° and 135°.

Figure 9:
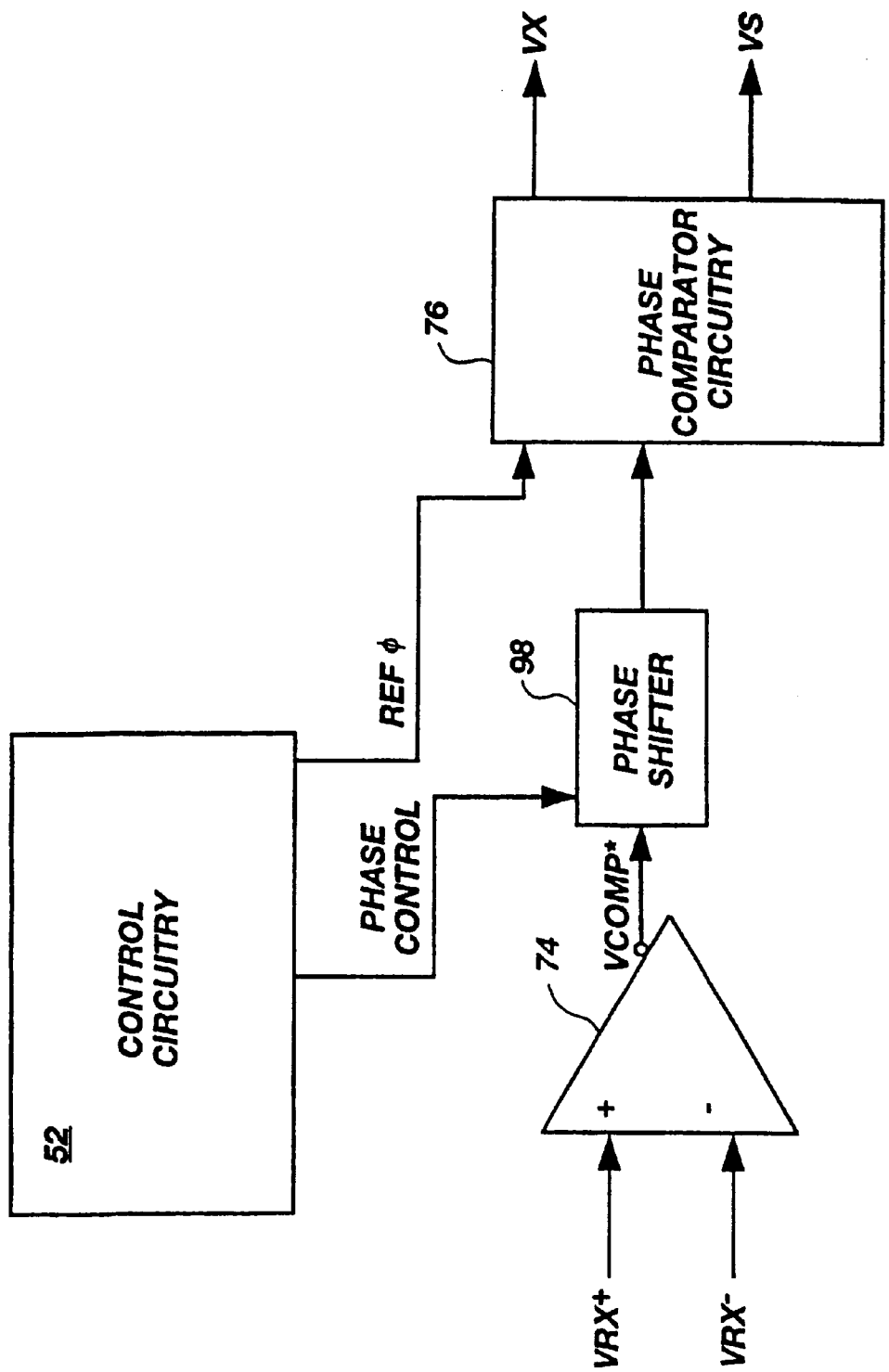
FIG. 9 is a block diagram of an alternative version of the flow metering circuit of FIG. 2.

As shown in FIG. 9, in an alternative version of the coarse adjustment described above, a phase shifter 98 interposed between the zero-crossing detector 74 and the phase comparator circuitry 76 shifts the signal VCOMP* by the 0°, 90°, 180°, or 270° described above in response to a PHASE CONTROL signal from the control circuitry 52 in order to maintain the XOR phase comparator in the phase comparator circuitry 76 in its accurate region between 45° and 135°. As a result, the timing signal REF0 may be supplied as the other input to the phase comparator circuitry 76 in place of the phase-variable reference signal REFS (not shown in FIG. 9). It should be understood from this alternative that any means for varying the phase shift presented to the phase comparator circuitry 76 to keep the circuitry 76 in a relatively accurate region for detection falls within the scope of the present invention.

"Fine" Temperature/Density Compensation in the Flow Metering Circuit

Figure 6:
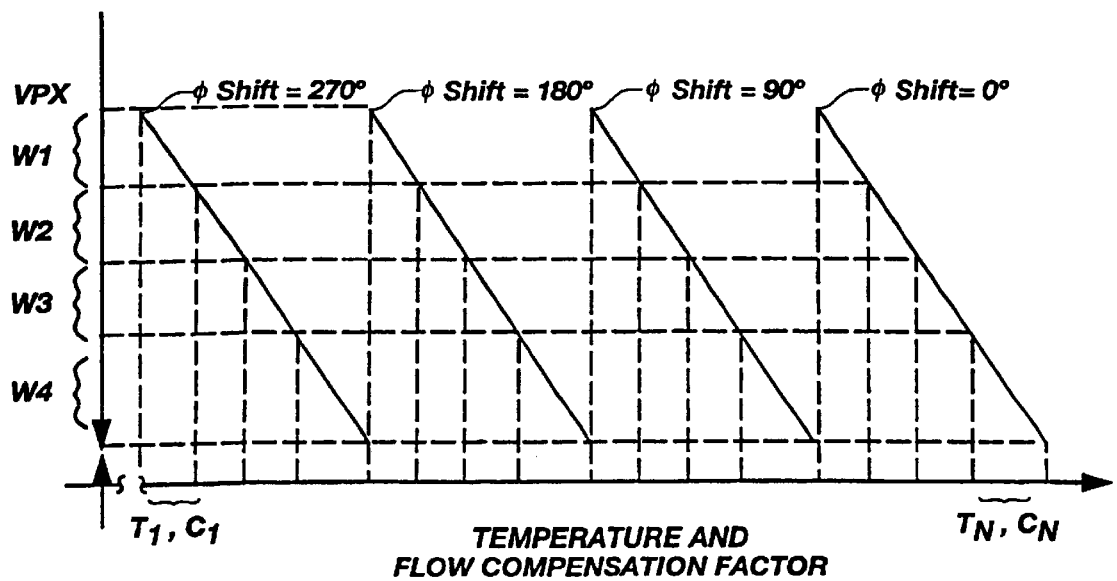
FIG. 6 is a graphical representation of a look-up table correlating the output voltage of the XOR phase comparator of FIG. 4 and cumulative "coarse" adjustments to the XOR phase comparator of FIGS. 5A to 5E to the temperature of the fluid under measurement, and to a compensation factor for flow measurement, in accordance with the present invention.

The coarse compensation for temperature/density described above is complimented in the preferred embodiment of the present invention by a form of "fine" compensation for temperature described herein. As shown in FIG. 6, using empirical measurement methods, a relationship can be established for any fluid 48 (FIG. 2) to be measured by the flow metering circuit 42 (FIG. 2) of the present invention between the averaged XOR phase comparison signal VPX, the cumulative phase shift $\phi_{shift}$ of the reference signal REFS by the control circuitry 52 (FIG. 2), and the temperature of the fluid 48. This relationship can then be used to determine a compensation factor to be applied to any measurements of flow of the fluid 48, and can be used to measure the temperature of the fluid 48, as will be described in more detail below.

As used herein, "cumulative" phase shift $\phi_{shift}$ means the total of the phase shifts in the reference signal REFS. Thus, for example, in FIGS. 5A, 5B, 5C, 5D, and 5E, the respective cumulative phase shifts $\phi_{shift}$ are 90°, 270°, 270°, 90°, and 180°.

Referring again to FIG. 6, "windows" W1, W2, W3, and W4, for example, may be established in a look-up table stored in the control circuitry 52 (FIG. 2) to correlate the averaged XOR phase comparison signal VPX, the cumulative phase shift $\phi_{shift}$, the temperature of the fluid 48 (FIG. 2) under measurement, and a flow compensation factor for use in conjunction with the measurements of fluid flow described below. The look-up table can be as follows:

TABLE 2

| $\phi_{shift}$ | Window (= f(VPX)) | Fluid Temperature | Flow Compensation Factor |
|---|---|---|---|
| 270° | W1 | $T_1$ | $C_1$ |
| ... | ... | ... | ... |
| 180° | W1 | $T_5$ | $C_5$ |
| ... | ... | ... | ... |
| 90° | W1 | T9 | C9 |
| ... | ... | ... | ... |
| 0° | W1 | $T_{N-3}$ | $C_{N-3}$ |
| ... | ... | ... | ... |
| | W4 | $T_N$ | $C_N$ |

Of course, the number of windows is not fixed at four, but, rather, may be varied within the scope of the present invention. Also, it should be understood that the values of temperature T and the compensation factors C in Table 2 are measured empirically and will vary from fluid to fluid.

Thus, for example, a flow measurement (to be described below) taken with a coarse temperature/density compensation of 270° (i.e., $\phi_{shift}$=270°) may be taken with the amplitude of the averaged XOR phase comparison signal VPX in window W1. Using the look-up table illustrated in Table 2 and stored in the control circuitry 52 (FIG. 2), the temperature of the fluid 48 (FIG. 2) under measurement may be determined to be $T_1$, and a flow compensation factor $C_1$ may be applied to the flow measurement (described below) to provide a level of fine compensation for temperature variations to the measurement.

Using both the coarse and fine adjustments described herein, it is believed accuracies to within approximately ±0.5% at flow rates of approximately 10 Liters per minute may be achieved.

Flow Measurement

Referring again to FIG. 2, a low-pass filter 80, such as a Sallen-Key low-pass filter, filters the XOR phase comparison signal VX (also shown in FIG. 3) and outputs a flow input signal SHA to a sample-and-hold (S/H) circuit 82. The flow input signal SHA and the switching signal FWDH are both shown in more detail in FIG. 7 in both the upstream and downstream switching states of the T/R switch 64. As can be seen from FIG. 7, the low-pass filter 80 causes the flow input signal SHA to rise exponentially toward an average of the XOR phase comparison signal VX.

Figure 7:
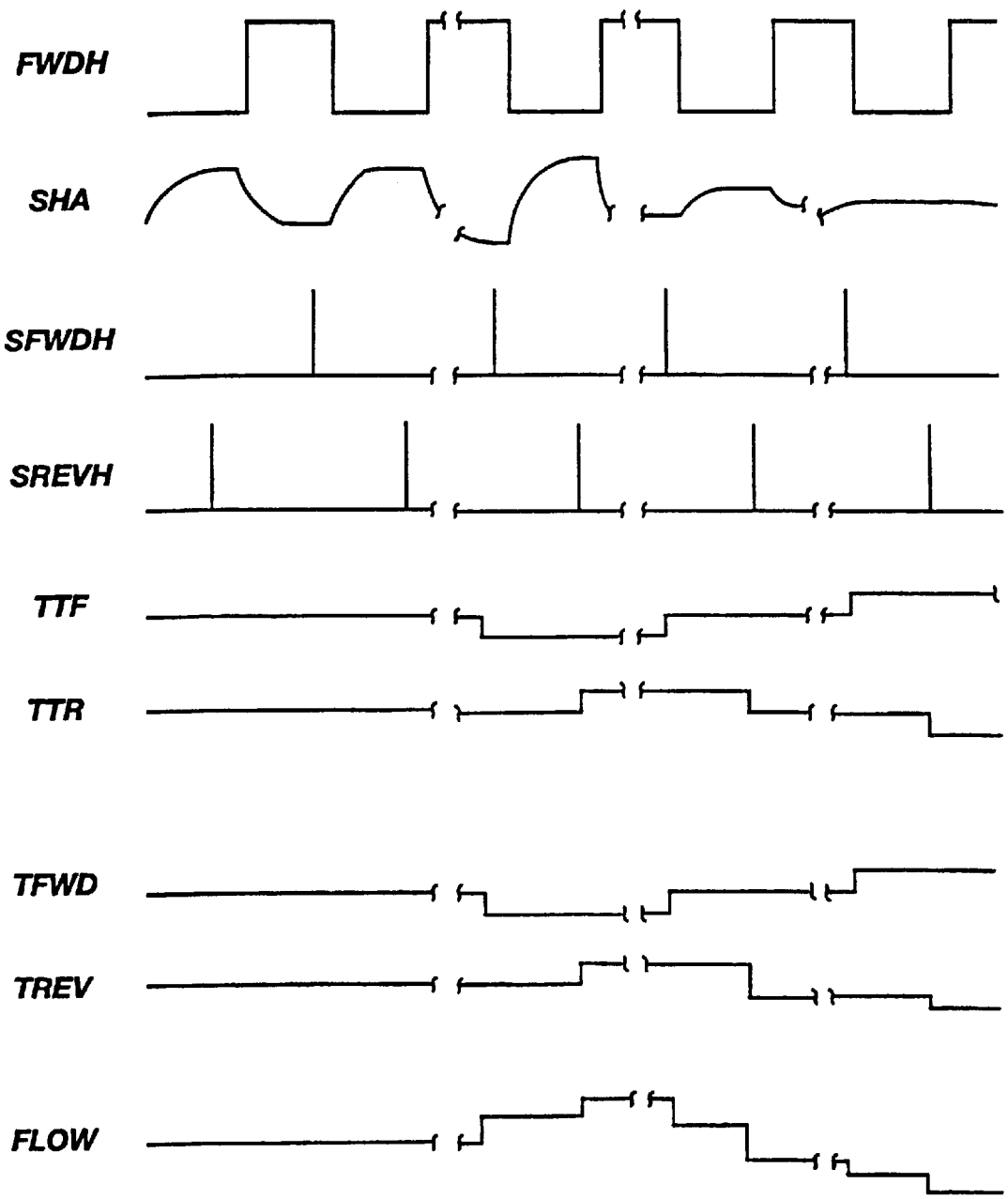
FIG. 7 is a timing diagram showing operation of a sample-and-hold circuit and its associated circuitry in the flow metering circuit of FIG. 2 to determine flow of the fluid under measurement in accordance with the present invention.

Referring to FIGS. 2 and 7, a 152 Hz forward sample signal SFWDH which pulses for about 1.8 microseconds (µs) about 2 milliseconds (ms) after each rising edge of the switching signal FWDH causes the S/H circuit 82 to sample and hold the amplitude of the flow input signal SHA resulting from each upstream measurement by the transducers 44 and 46. This "held" forward amplitude is output from the S/H circuit 82 as a forward held signal TTF. Level translation and scaling circuitry 84 then outputs a translated and scaled forward held signal TFWD corresponding to the forward held signal TTF for use by the control circuitry 52.

Similarly, a 152 Hz reverse sample signal SREVH which pulses for about 1.8 microseconds (µs) about 2 milliseconds (ms) after each falling edge of the switching signal FWDH causes the S/H circuit 82 to sample and hold the amplitude of the flow input signal SHA resulting from each downstream measurement by the transducers 44 and 46. This held reverse amplitude is output from the S/H circuit 82 as a reverse held signal TTR. The level translation and scaling circuitry 84 then outputs a translated and scaled reverse held signal TREV corresponding to the reverse held signal TTR for use by the control circuitry 52.

The forward and reverse held signals TTF and TTR are also input to an instrumentation amplifier 86 which amplifies the difference between the two signals and provides an output 88 indicative of the flow of the fluid 48 in the conduit 50. The level translation and scaling circuitry 84 then outputs a translated and scaled FLOW signal for use by the control circuitry 52.

It should be understood that the control circuitry 52 may directly use the signal FLOW to indicate the flow of the fluid 48, or may, instead, calculate the flow of the fluid 48 from the signals TFWD and TREV. It should also be understood that the control circuitry 52 may apply a compensation factor, determined as described above, to the signal FLOW or to any calculation of flow derived from the signals TFWD and TREV.

Air-In-Line Detection

Figure 8B:
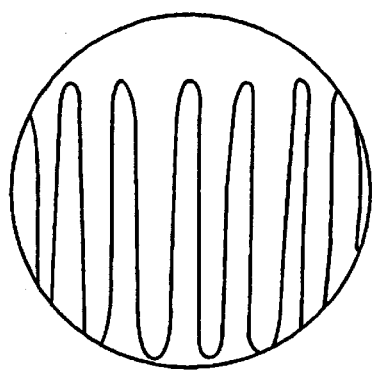
FIGS. 8A and 8B are timing diagrams showing operation of bubble detection circuitry in the flow metering circuit of FIG. 2.
Figure 8A:
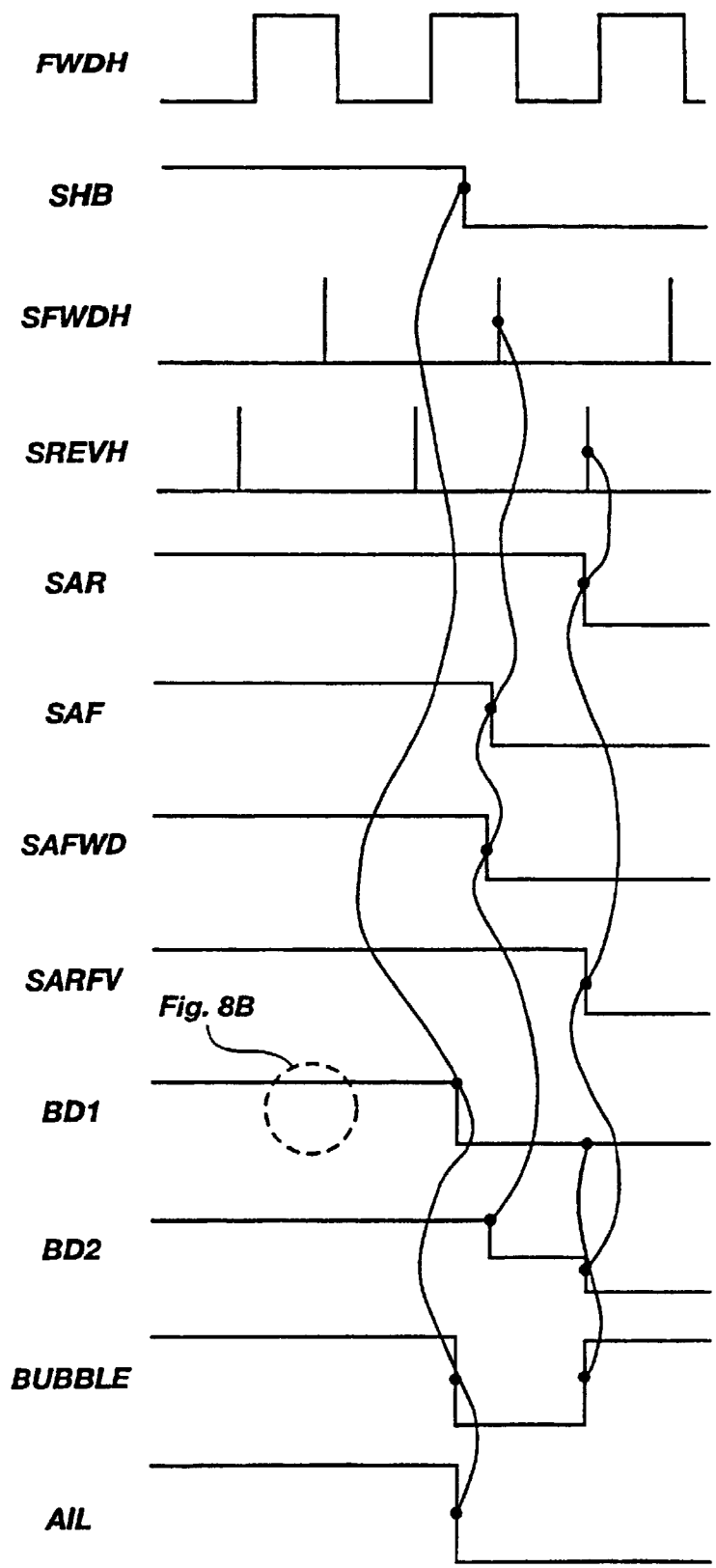

Referring to FIGS. 2, 8A, and 8B, it is often desirable to be able to detect anomalies in a fluid 48 under measurement. For example, if the fluid 48 under measurement is blood from a patient circulating in extra-corporeal tubing during a medical procedure, it is clearly hazardous to the patient's health if an air bubble is introduced into the patient.

Therefore, the present invention provides air-in-line detection as follows. A peak detector 90 receives the filtered output signal VRX⁻ (also shown in FIG. 3) and outputs an attenuated version thereof as a fast air-in-line detect signal BD1. Although FIG. 8A shows the fast air-in-line detect signal BD1 at DC levels because of the time period depicted in FIG. 8A, it should be understood that the signal BD1 is, in fact, a 2.5 MHZ signal, as is shown in FIG. 8B. It should be noted that an anomaly in the fluid 48 passing through the conduit 50, such as an air bubble, will cause a rapid change in the amplitude of the filtered output signal VRX⁻, and hence in the amplitude of the fast air-in-line detect signal BD1, because ultrasonic signals are attenuated differently by the anomaly than they are by the fluid 48. In the example of an air bubble, the ultrasonic signals are attenuated much more by the air than they are by the blood.

The peak detector 90 also outputs an air-in-line detect input signal SHB to the S/H circuit 82. The air-in-line detect input signal SHB and the switching signal FWDH are both shown in more detail in FIG. 8A in both the upstream and downstream switching states of the T/R switch 64. As can be seen from FIG. 8A, the peak detector 90 causes the air-in-line detect input signal SHB to "ride the peaks," so to speak, of the filtered output signal VRX$^-$.

Referring to FIGS. 2 and 8A, the 152 Hz forward sample signal SFWDH causes the S/H circuit 82 to sample and hold the amplitude of the air-in-line detect input signal SHB resulting from each upstream measurement by the transducers 44 and 46. This held forward amplitude is output from the S/H circuit 82 as a forward sampled signal SAF. The level translation and scaling circuitry 84 then outputs a translated and scaled forward sampled signal SAFWD corresponding to the forward sampled signal SAF for use by the control circuitry 52.

Similarly, the 152 Hz reverse sample signal SREVH causes the S/H circuit 82 to sample and hold the amplitude of the air-in-line detect input signal SHB resulting from each downstream measurement by the transducers 44 and 46. This held reverse amplitude is output from the S/H circuit 82 as a reverse sampled signal SAR. The level translation and scaling circuitry 84 then outputs a translated and scaled reverse sampled signal SAREV corresponding to the reverse sampled signal SAR for use by the control circuitry 52.

The forward and reverse sampled signals SAF and SAR are also input to a summing amplifier 92 which averages the two signals and provides a slow air-in-line detect signal BD2 as an output. It should be understood that the slow air-in-line detect signal BD2 changes in amplitude relatively slowly in comparison to the fast air-in-line detect signal BD1 because of the delays inherent in the S/H circuit 82.

The fast and slow air-in-line detect signals BD1 and BD2 are presented to an amplitude comparator 94, which outputs a high air-in-line detect signal BUBBLE when the amplitudes of the signals BD1 and BD2 are equal and outputs a briefly low air-in-line detect signal BUBBLE when the amplitudes are not equal. A one-shot circuit 96 then "stretches" the width of any low pulses in the air-in-line detect signal BUBBLE indicative of a detected anomaly in the fluid 48 and then outputs the stretched signal as an air-in-line signal AIL to the control circuitry 52. The one-shot circuit 96 stretches low pulses in the air-in-hine detect signal BUBBLE so they are more readily detected by the control circuitry 52.

It should be understood that the control circuitry 52 may directly use the signal AIL to indicate an anomaly in the fluid 48, and may also determine the presence of an anomaly using the signals SAFWD and SAREV. It should also be understood that the present invention is intended to include within its scope detection of any anomaly, not just air bubbles in blood as described herein.

An example of the detection of an air bubble may be understood in reference to FIGS. 2 and 8A. An air bubble (not shown) passing through the conduit 50 causes a momentary drop in the amplitude of the filtered output signal VRX$^-$, which causes a corresponding drop in the amplitude of the fast air-in-line detect signal BD1 as shown in FIG. 8A. The drop in the signal BD1 causes a corresponding drop in the air-in-line detect input signal SHB and in the air-in-line detect signal BUBBLE, which, in turn, causes a drop in the air-in-line signal AIL.

The forward sample signal SFWDH then causes the S/H circuit 82 to sample and hold the reduced air-in-line detect input signal SHB. As a result, the forward sampled signal SAF and the translated and scaled forward sampled signal SAFWD also drop. The reduced forward sampled signal SAF then causes a reduction in the slow air-in-line detect signal BD2.

Next, the reverse sample signal SREVH causes the S/H circuit 82 to sample and hold the reduced air-in-line detect input signal SB1. As a result, the reverse sampled signal SAR and the translated and scaled reverse sampled signal SAREV also drop. The reduced forward sampled signal SAR then causes a further reduction in the slow air-in-line detect signal BD2. Because BD1 and BD2 are again equal, the air-in-line detect signal BUBBLE goes high again, while the air-in-line signal AIL remains low as a result of the one-shot circuit 96 stretching the low pulse in the air-in-line detect signal BUBBLE as described above.

The Control Circuitry

Figure 11A:
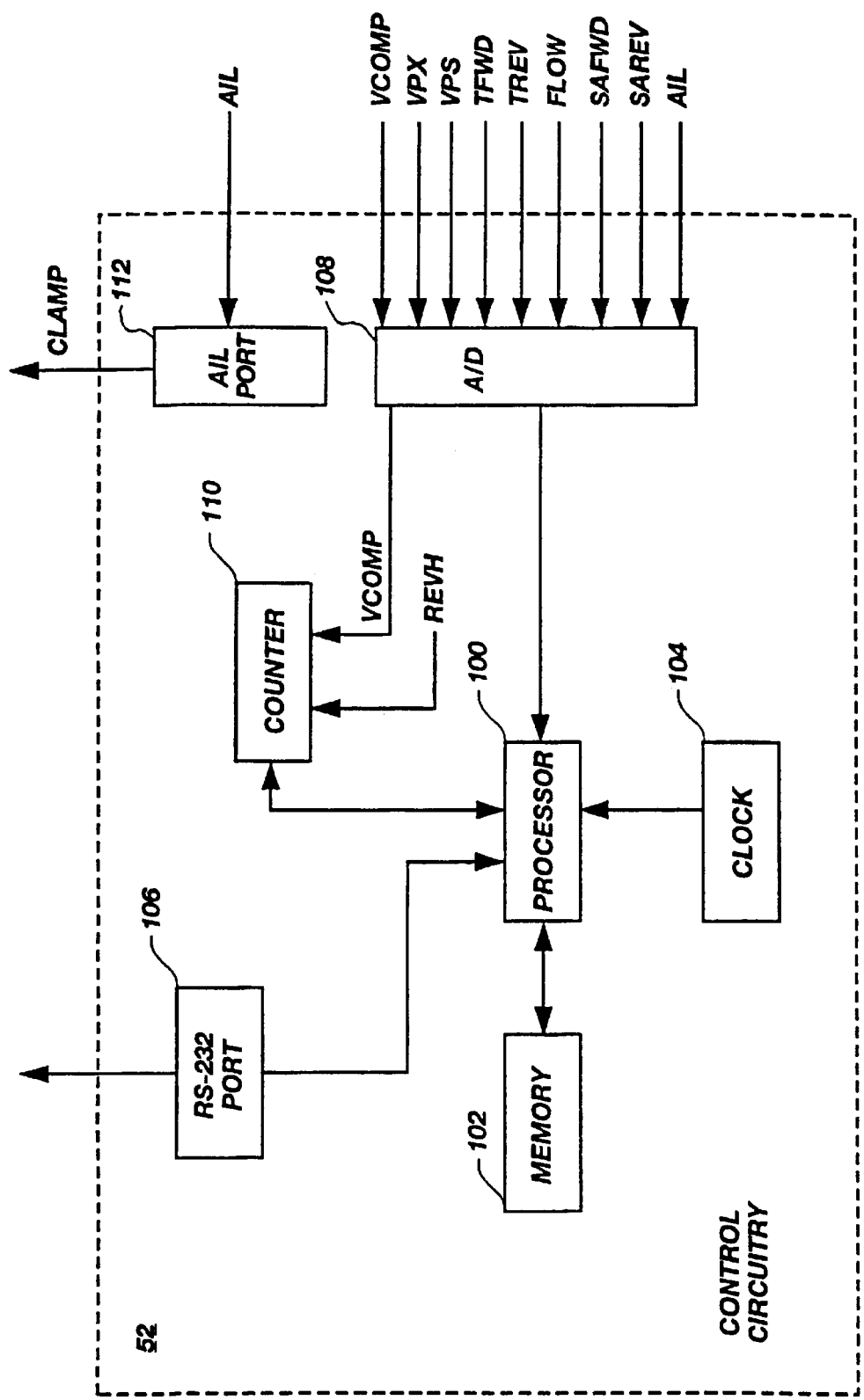
FIGS. 11A and 11B are respective block and timing diagrams showing control circuitry in the flow metering circuit of FIG. 2 in more detail.

As shown in FIG. 11A, the control circuitry 52 includes a processor 100, memory device 102, clock 104, RS-232 serial port 106 for communications between the control circuitry 52 and external electronic devices (not shown), an analog-to-digital (A/D) converter 108, a counter 110, and an air-in-line port 112 for providing a clamping signal CLAMP to an external clamping device (not shown in FIG. 11A) in response to the air-in-line signal AIL, as will be described in more detail below with respect to FIG. 12.

Measurement of Actual Transit Time to Determine Flow and Temperature

Figure 11B:
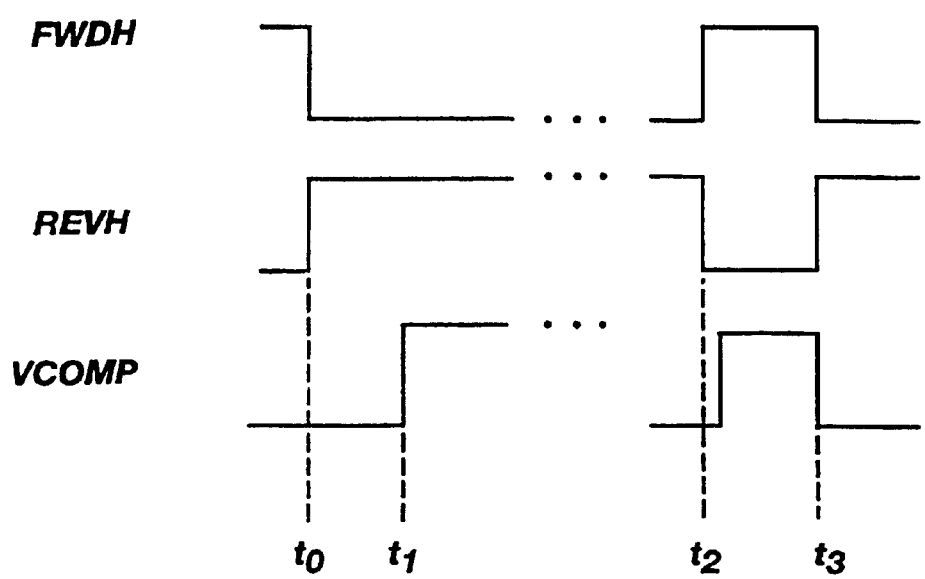

With reference to FIGS. 11A and 11B, the counter 110 receives the crossing detect signal VCOMP and the inverse REVH of the switching signal FWDH described above. The counter 110 begins counting at time to at the positive-going edge of the REVH signal, indicating the initiation of the downstream switching state in the T/R switch 64 (FIG. 2), and stops counting at time $t_1$ at the first positive-going edge of the crossing detect signal VCOMP. Because of the configuration of the flow metering circuit 42 (FIG. 2), the time counted by the counter 110 between the times $t_0$ and $t_1$ is substantially equal to the transit time of ultrasonic signals downstream through the fluid 48 FIG. 2).

The counter 110 begins counting again at time $t_2$ at the negative-going edge of the REVH signal, indicating the initiation of the upstream switching state in the T/R switch 64 (FIG. 2), and stops counting at time $t_3$ at the first negative-going edge of the crossing detect signal VCOMP. Because of the configuration of the flow metering circuit 42 (FIG. 2), the time counted by the counter 110 between the times $t_2$ and $t_3$ is substantially equal to the transit time of ultrasonic signals upstream through the fluid 48 (FIG. 2).

The counter 110 provides both its upstream and downstream time counts to the processor 100, which can then calculate the flow of the fluid 48 (FIG. 2) directly from these time counts. Either time count is also sufficient for the processor 100 to calculate the speed of sound in the fluid 48 and, hence, the temperature of the fluid 48.

Application

Figure 12:
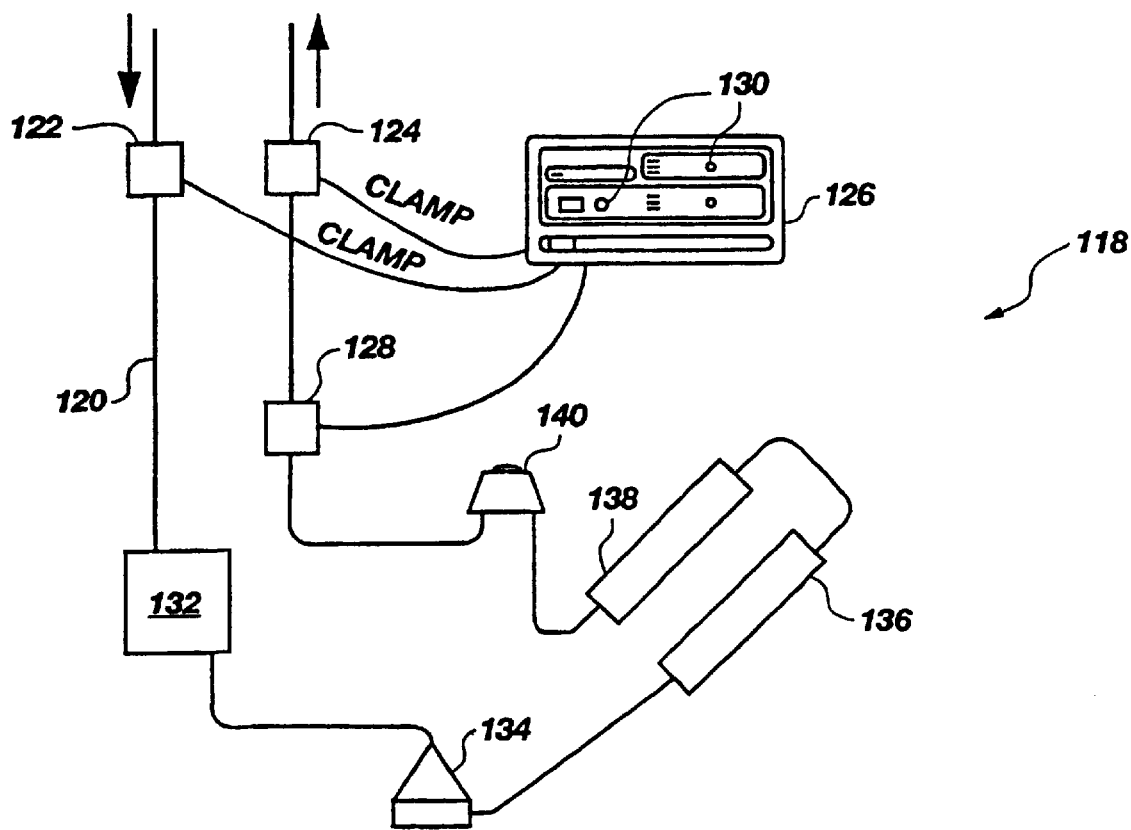
FIG. 12 is a block diagram showing a preferred embodiment of the present invention directed to a transit time flow metering system for monitoring extra-corporeal blood flow.

As shown in FIG. 12, an extra-corporeal blood flow system 118 for use in medical procedures includes tubing 120 connected to the venous and arterial blood flows of a patient (not shown) for oxygenating and then returning blood to the patient. The tubing 120 may be any tubing commonly used for medical purposes, including, for example, Tygon® tubing. Clamps 122 and 124, such as those pneumatically-driven clamps described and claimed in U.S. Pat. No. 5,445,613 to Orth (assigned to the Assignee of the present invention, Rocky Mountain Research, Inc. of Salt Lake City, Utah), are activated by a control box 126 including the flow metering circuit 42 of FIG. 2.

Specifically, the control box 126 activates one or more of the clamps 122 and 124 to prevent blood flow in the tubing 120 when air or reverse flow is detected in the tubing 120 by ultrasonic transducers 128 and the flow metering circuit 42 (FIG. 2). It is also contemplated that clamps powered by a solenoid or hydraulic source are also useable with the present invention.

In addition, the control box 126 includes visual and/or audible alarms 130 for indicating to medical personnel that an air bubble is in the tubing 120, that reverse flow has occurred in the tubing 120, or that low flow is present (less than about 500 mL/minute). The system 118 also includes a venous reservoir 132, a pump 134, an oxygenator 136, a heat exchanger 138, and an arterial filter 140. The pump 134 may be, for example, a centrifugal or peristaltic pump, a rotary vane pump, a magnetically-driven frictionless pump, or any other means for moving a fluid through a conduit.

Although the present invention has been described with reference to particular embodiments, the invention is not limited to these embodiments. For example, while various steps of these embodiments have been described as occurring in a particular order, it will be understood that these steps need not necessarily occur in the described order to fall within the scope of the present invention. Thus, the invention is limited only by the appended claims, which include within their scope all equivalent devices and methods that operate according to the principles of the invention as described.

What is claimed is:

1. A flow measuring apparatus comprising:
    an assembly for transmitting, in first and second directions, ultrasonic signals through fluid in a conduit and for receiving the transmitted ultrasonic signals transmitted in each of the first and second directions;
    circuitry operably coupled to the transmitting and receiving assembly for detecting phase shifts in the received ultrasonic signals relative to the ultrasonic signals transmitted in each of the first and second directions, the phase shift detecting circuitry configured to have a plurality of detection ranges each spanning substantially less than 360° and falling between 0° and 360° including an accuracy range wherein a physical response of said phase shift detecting circuitry to a phase shift occurring in said accuracy range is more accurate relative to a physical response of said phase shift detecting circuitry to a phase shift occurring in another of said plurality of detection ranges; and
    circuitry operably coupled to the phase shift detecting circuitry and configured for adjusting phase shifts in the received ultrasonic signals for detection by the phase shift detection circuitry in response to already-detected phase shifts in the received ultrasonic signals to enhance accurate detection of phase shifts by maintaining phase shifts detected by the phase shift detecting circuitry within said accuracy range of the phase shift detecting circuitry.

2. The flow measuring apparatus of claim 1 wherein the assembly for transmitting, in first and second directions, an ultrasonic signal through fluid in a conduit and for receiving the transmitted ultrasonic signals transmitted in each of the first and second directions is configured for operation with a fluid selected from at least one of a liquid and a gas.

3. The flow measuring apparatus of claim 1 wherein the assembly for transmitting, in first and second directions, an ultrasonic signal through fluid in a conduit and for receiving the transmitted ultrasonic signals transmitted in each of the first and second directions comprises at least two ultrasonic transducers.

4. Flow measuring circuitry for use in a flow measuring apparatus having an assembly for transmitting, in first and second directions, ultrasonic signals through fluid in a conduit and for receiving the transmitted ultrasonic signals transmitted in each of the first and second directions, the flow measuring circuitry comprising:
    circuitry for detecting phase shifts in the received ultrasonic signals relative to the ultrasonic signals transmitted in each of the first and second directions, the phase shift detecting circuitry configured to have a plurality of detection ranges each spanning substantially less than 360° and falling between 0° and 360° including an accuracy range wherein a physical response of said phase shift detecting circuitry to a phase shift occurring in said accuracy range is more accurate relative to a physical response of said phase shift detecting circuitry to a phase shift occurring in another of said plurality of detection ranges; and
    circuitry coupled to the phase shift detecting circuitry and configured for adjusting phase shifts in the received ultrasonic signals for detection by the phase shift detecting circuitry in response to already-detected phase shifts in the received ultrasonic signals to enhance accurate detection of phase shifts by maintaining phase shifts detected by the phase shift detecting circuitry within said accuracy range of the phase shift detecting circuitry.

5. The flow measuring circuitry of claim 4 wherein the phase shift detecting circuitry includes an amplifier, a zero-crossing detector, and at least one phase comparator.

6. The flow measuring circuitry of claim 5 wherein the at least one phase comparator is selected from a group comprising a Set-Reset (SR) flip-flop phase comparator and an exclusive-OR (XOR) phase comparator.

7. The flow measuring circuitry of claim 4 wherein the phase shift detection adjusting circuitry comprises a microprocessor, memory circuitry, a clock, and an analog-to-digital converter.

8. The flow measuring circuitry of claim 4 wherein the phase shift detecting circuitry comprises circuitry for driving a comparison signal at a selected phase relative to a received ultrasonic signal and for detecting phase shifts in the comparison signal relative to a reference signal, wherein the phase shift detection adjusting circuitry comprises circuitry for providing the reference signal to the phase shift detecting circuitry at a selected phase relative to a transmitted ultrasonic signal and for adjusting the selected phase of at least one of the comparison and reference signals in response to detected phase shifts in the comparison signal relative to the reference signal to enhance the accurate detection of phase shifts by maintaining phase shifts detected by the phase shift detecting circuitry within said accuracy range of the phase shift detection circuitry.

9. The flow measuring circuitry of claim 8 wherein the phase shift detection adjusting circuitry comprises circuitry for adjusting the selected phase of the at least one of the comparison and reference signals by at least one of zero, ninety, one-hundred eighty, and two-hundred seventy degrees in response to detected phase shifts.

10. The flow measuring circuitry of claim 8 further comprising circuitry coupled to the phase shift detecting circuitry and to the phase shift detection adjusting circuitry for correlating detected phase shifts in the comparison signal relative to the reference signal to a flow rate of the fluid in the conduit, wherein the phase shift detection adjusting circuitry further comprises circuitry for correlating cumulative adjustments to the selected phase of the at least one of the comparison and reference signals, together with the detected phase shifts in the comparison signal relative to the reference signal, to predetermined flow rate correction factors to be applied to the flow rate to compensate for phase shifts in the received ultrasonic signal attributable to at least one parameter associated with the fluid in the conduit other than flow rate so as to enhance accurate correlation of detected phase shifts in the comparison signal to the flow rate.

11. The flow measuring circuitry of claim 10 wherein the phase shift detection adjusting circuitry further comprises circuitry for storing the predetermined flow rate correction factors in a look-up table.

12. The flow measuring circuitry of claim 10 wherein the phase shift detection adjusting circuitry further comprises circuitry for determining temperature of the fluid by correlating the cumulative adjustments to the selected phase of the at least one of the comparison and reference signals, together with the detected phase shifts in the comparison signal relative to the reference signal, to the temperature of the fluid.

13. The flow measuring circuitry of claim 12 wherein the phase shift detection adjusting circuitry further comprises circuitry for storing, in a look-up table, a plurality of predetermined flow compensation factors relating to determined temperature of the fluid.

14. The flow measuring circuitry of claim 4 further comprising circuitry for starting a transit time count upon the initiation of transmission of the ultrasonic signal through the fluid and for stopping the transit time count upon reception of the transmitted ultrasonic signal.

15. The flow measuring circuitry of claim 14 wherein the transit time count circuitry includes a digital counter.

16. The flow measuring circuitry of claim 14 further comprising circuitry coupled to the transit time count circuitry for correlating transit time counts to a flow rate of the fluid in the conduit.

17. The flow measuring circuitry of claim 14 further comprising circuitry coupled to the transit time count circuitry for correlating transit time counts to a temperature of the fluid in the conduit.

18. The flow measuring circuitry of claim 4, further comprising circuitry for detecting anomalies in the fluid, the anomaly detection circuitry comprising:
   circuitry operably coupled to the transmitting and receiving assembly for outputting a first anomaly detection signal that changes relatively rapidly in response to variations in amplitude of the received ultrasonic signals;
   sample-and-hold circuitry operably coupled to the transmitting and receiving assembly for sampling amplitudes of the received ultrasonic signals and for outputting a second anomaly detection signal that changes relatively slowly in response to variations in amplitude of the received ultrasonic signals; and
   circuitry operably coupled to the rapidly changing anomaly detection signal outputting circuitry and the sample-and-hold circuitry for detecting differences between the rapidly changing and slowly changing anomaly detection signals indicative of anomalies in the fluid.

19. The flow measuring apparatus of claim 18 wherein the rapidly changing anomaly detection signal outputting circuitry includes an amplifier and a Resistor-Capacitor (RC) network.

20. The flow measuring apparatus of claim 18 wherein the transmitting and receiving assembly comprises first and second ultrasonic transducers and wherein the sample-and-hold circuitry comprises:
   a first sample-and-hold circuit for sampling and holding an ultrasonic signal received by the first ultrasonic transducer and transmitted by the second ultrasonic transducer;
   a second sample-and-hold circuit for sampling and holding an ultrasonic signal received by the second ultrasonic transducer and transmitted by the first ultrasonic transducer; and
   summing circuitry operably coupled to the first and second sample-and-hold circuits for outputting the relatively slowly changing anomaly detection signal.

21. The flow measuring apparatus of claim 18 wherein the difference detecting circuitry comprises an amplitude comparator and a one-shot circuit.

22. An apparatus for conducting a fluid while measuring flow of the fluid, the apparatus comprising:
   a fluid conduit through which the fluid may flow;
   an assembly disposed proximate the fluid conduit for transmitting ultrasonic signals in a first and a second direction through the fluid in the conduit and for receiving the transmitted ultrasonic signals;
   circuitry operably coupled to the transmitting and receiving assembly for detecting phase shifts in the received ultrasonic signals relative to the ultrasonic signals transmitted in each of the first and second directions, the phase shift detecting circuitry configured to have a plurality of detection ranges each spanning substantially less than 360° and falling between 0° and 360° including an accuracy range wherein a physical response of said phase shift detecting circuitry to a phase shift occurring in said accuracy range is more accurate relative to a physical response of said phase shift detecting circuitry to a phase shift occurring in another of said plurality of detection ranges; and
   circuitry coupled to the phase shift detecting circuitry and configured for adjusting phase shifts in the received ultrasonic signal for detection by the phase shift detecting circuitry in response to already-detected phase shifts in the received ultrasonic signal to enhance accurate detection of phase shifts by maintaining phase shifts detected by the phase shift detecting circuitry within said accuracy range of the phase shift detecting circuitry.

23. The fluid conducting apparatus of claim 22 wherein the fluid conduit is selected from a group comprising tubing, a conduit associated with a hull of a marine vessel, a flare stack inlet pipe, an air inlet of an engine, a fuel inlet of an engine, a drilling rig conduit, a conduit for carrying hydrocarbon fluids, a chemical conduit, a conduit for carrying a bodily fluid and an open-channel conduit.

24. An extracorporeal blood flow system comprising:
   a blood conduit connectable to a patient for diverting blood from, and later returning blood to, the patient;
   a pump in communication with the blood conduit for pumping blood therethrough; and
   a flow measuring apparatus including:
      an assembly disposed proximate the fluid conduit for transmitting ultrasonic signals in a first and a second direction through the fluid in the conduit and for receiving the transmitted ultrasonic signals;
      circuitry operably coupled to the transmitting and receiving assembly for detecting phase shifts in the received ultrasonic signals relative to the ultrasonic signals transmitted in each of the first and second directions, the phase shift detecting circuitry configured to have a plurality of detection ranges each spanning substantially less than 360° and falling between 0° and 360° including an accuracy range wherein a physical response of said phase shift detecting circuitry to a phase shift occurring in said accuracy range is more accurate relative to a physical response of said phase shift detecting circuitry to a phase shift occurring in another of said plurality of detection ranges; and circuitry operably coupled to the phase shift detecting circuitry for adjusting phase shifts in the received ultrasonic signal for detection by the phase shift detecting circuitry in response to already-detected phase shifts in the received ultrasonic signal to enhance accurate detection of phase shifts by maintaining phase shifts detected by the phase shift detecting circuitry within said accuracy range of the phase shift detecting circuitry.

25. The extracorporeal blood flow system of claim 24 wherein the blood conduit comprises tubing.

26. The extracorporeal blood flow system of claim 24 wherein the pump is selected from a group comprising a centrifugal pump, a peristaltic pump, a rotary vane pump, and a magnetically-driven frictionless pump.

27. The extracorporeal blood flow system of claim 24 further comprising a clamp disposed proximate the blood conduit and operably positioned with respect to the flow metering apparatus for clamping the blood conduit closed responsive to a parameter associated with the blood detected by the flow metering apparatus.

28. The extracorporeal blood flow system of claim 27 wherein the clamp comprises a pneumatically-driven clamp.

29. The extracorporeal blood flow system of claim 24 further comprising a venous reservoir, an oxygenator, a heat exchanger, and an arterial filter in communication with the blood conduit.

30. In a flow measuring apparatus including ultrasonic transducers for transmitting an ultrasonic signal through a fluid in a conduit and for receiving the transmitted ultrasonic signal, circuitry for generating comparison and reference signals having selected phase relationships with the respective received and transmitted ultrasonic signal, and circuitry for detecting phase shifts in the comparison signal relative to the reference signal, the phase shift detecting circuitry having an accuracy range spanning substantially less than 360° and falling between 0° and 360° wherein a physical response of said phase shift detecting circuitry to a phase shift occurring in said accuracy range is more accurate relative to a physical response of said phase shift detecting circuitry to a phase shift occurring outside of said accuracy range, a method for maintaining the phase shift detecting circuitry in its accuracy range, the method comprising adjusting a phase of at least one of the comparison and reference signals so the phase shift detected by the phase shift detecting circuitry falls within the accuracy range thereof.

31. The method of claim 30 wherein the step of adjusting the phase of at least one of the comparison and reference signals comprises adjusting the phase of at least one of the comparison and reference signals by one of zero, ninety, one-hundred eighty, and two-hundred seventy degrees.

32. A flow measuring method comprising:

transmitting ultrasonic signals through a fluid in a conduit in two directions; receiving the transmitted ultrasonic signals;

detecting phase shifts in the received ultrasonic signals relative to the transmitted ultrasonic signals;

correlating the detected phase shifts to flow of the fluid in the conduit; and adjusting the detection of phase shifts in response to previously detected phase shifts so as to enhance the accuracy of the correlation of the detected phase shifts to at least one of a flow rate of the fluid and a temperature of the fluid by maintaining phase shifts to be detected within an accuracy range due to the physical response of phase shift detecting circuitry, said accuracy range spanning substantially less than 360° and falling between 0° and 360° wherein phase shifts are detected with more accuracy relative to phase shifts occurring outside said accuracy range.

33. The flow measuring method of claim 32 wherein the step of transmitting the ultrasonic signals through the fluid comprises transmitting the ultrasonic signals upstream and downstream through the fluid, wherein the step of receiving comprises receiving the upstream and downstream transmitted ultrasonic signals, wherein the step of detecting phase shifts comprises detecting phase shifts in the received upstream ultrasonic signal relative to the upstream transmitted ultrasonic signal and detecting phase shifts in the received downstream ultrasonic signal relative to the downstream transmitted ultrasonic signal, wherein the step of correlating comprises determining a difference between the detected upstream and downstream phase shifts and correlating the determined differences to the at least one of the flow rate and the temperature of the fluid in the conduit.

\* \* \* \* \*